United States Patent [19]
Sugiki et al.

[11] Patent Number: 4,904,593
[45] Date of Patent: Feb. 27, 1990

[54] NOVEL MICROORGANISM, A NOVEL ESTERASE AND METHOD FOR PREPARING THE SAME

[75] Inventors: Chiaki Sugiki; Kanji Nishizawa, Hyogo; Masako Sugimoto, Hyogo; Kazumi Sonoda, Hyogo; Fumitaka Kishimoto, Hyogo, all of Japan

[73] Assignee: Sumitomo Chemical Company, Limited, Osaka

[21] Appl. No.: 41,290

[22] Filed: Apr. 22, 1987

[30] Foreign Application Priority Data

Apr. 22, 1986 [JP] Japan .................................. 61-92595
Jun. 24, 1986 [JP] Japan ................................ 61-147452

[51] Int. Cl.$^4$ .................... C12N 9/18; C12N 1/20; C12R 1/07
[52] U.S. Cl. .............................. 435/197; 435/252.5; 435/832
[58] Field of Search ............. 435/197, 253, 832, 252.5

[56] References Cited

U.S. PATENT DOCUMENTS 3,972,774  8/1976  Brannon ................................ 195/29

FOREIGN PATENT DOCUMENTS 60-30681  2/1985  Japan .
60-145096 7/1985  Japan .
3418374A 10/1985  Japan .

OTHER PUBLICATIONS

Abernathy, C. O., et al. (1973) Science 179, 1235–1236.
Riddles, P. W., et al. (1983) Anal. Biochem. 132, 105–109.
Matsunaga et al., "Chemical Abstracts", vol. 80, No. 15, p. 112, No. 79488y (1974).
Riefler, III, "Microbiology Abstracts", vol. 11, No. 9, No. 11A6024 (1976).
Higerd et al. "Chemical Abstracts", vol. 79, No. 5, p. 183, No. 28802t (1973).
"Immobilized Porcine Liver Esterase: A Convenient Reagent for the Preparation of Chiral Building Blocks", Tetrahedron Letters, vol. 26, No. 4, pp. 407–410 (1985) by Laumen et al.
"Enzymatic Syntheses of Chiral Building Blocks from Racemates: Preparation of (1R,3R)-Chrysanthemic-,-Permethrinic and -Caronic Acids from Racemic, Diastereomeric Mixtures", Agnew. Chem. Int. Ed. Engl. 23 (1984) No. 1, by Schneider et al.
"Enzymatic Syntheses of Chiral Building Blocks from Prochiral meso-Substrates: Preparation of Methyl(hydrogen)-1,2-cycloalkanedicarboxylates", Agnew. Chem. Int. Ed. Engl. 23 (1984) No. 1, by Schneider et al.
"Enzymes in Organic Synthesis, 35, Stereoselective Pig Liver Esterase Catalyzed Hydrolyses of 3-Substituted Glutarate Diesters, Optimization of Enantiomeric Excess via Reaction Conditoins Control", J. Org. Chem. 1986, 51, 2047–2050 by Lam et al.
"Enzymes in Organic Synthesis, 33, Stereoselective pig liver esterase-catalyzed hydrolyses of meso cyclopentyl-, tetrahydrofuranyl-, and tetrahydrothiophenyl-1,3-diesters", Can. J. Chem. 63, 452 (1985), by Jones et al.
"Asymmetric Hydrolysis of Prochiral Diesters with Pig Liver Esterase, Preparation of Optically Active Intermediates for the Synthesis of (+)-Biotin and (+)-α-Methyl-3,4-dihydroxy-phenylalanine", Agric. Biol. Chem., 46 (7), 1907–1910, (1982) by Iriuchijima et al.

(List continued on next page.)

Primary Examiner—Thomas G. Wiseman
Assistant Examiner—Charles L. Patterson
Attorney, Agent, or Firm—Birch, Stewart, Kolasch and Birch

[57] ABSTRACT

A novel esterase (molecular weight 54,000±2,000) derived from a microorganism belonging to genus Bacilus is extensively utilizable for organic synthetic reaction, especially for asymmetric hydrolysis of ethyl 2,2-dimethyl-3-(2,2-dichlorovinyl)cyclopropane carboxylate (ethyl permethrate), in the same manner as pig liver esterase.

The microorganism suitable for production of the above novel esterase is Bacillus sp. DC-1 (FERM BP-1254).

2 Claims, 4 Drawing Sheets

OTHER PUBLICATIONS

"Asymmetric Hydrolysis of Prochiral Dimethyl 3-Benzyloxycarbonylaminoglutarate with Microorganisms, Preparation of (S)-3-Amino-4-methoxycarbonylbutyric Acid for the Synthesis of Carbapenem and Negamycin Antibiotics", Agric. Biol. Chem., 47(6), 1363–1365, (1983) by Kotani et al.

"Preparation of Optically Active 2,2'-Dihydroxy-1,1'-binaphthyl via Microbial Resolution of the Corresponding Racemic Diester", J. Chem. Soc., Chem. Commun., 1985, by Fujimoto et al.

"Bifunctional Chiral Synthons via Biochemical Methods, Optically-Active 2,2'-dihydroxy 1,1'-Binaphthyl", Tetrahedron Lett. 26 4323–4326 (1985), by Wu et al.

"De-Esterification of Cephalosporin Para-Nitrobenzyl Esters by Microbial Enzymes", The Journal of Antibiotics, Fed. 1976, by Brannon et al.

"Purification of Four Esterases from Aspergillus niger NRRL 337", Agric. Biol. Chem., 47(8), 1865–1868, 1983 by Iwai et al.

"Physical Properties and Kinetic Behavior of a Cephalosporin Acetylesterase Produced by Bacillus subtilis", Applied Microbiology, Sep. 1975, pp. 413–419, by Abbott et al.

"Purification and some properties of a phthalate ester hydrolyzing enzyme from Nocardia erythropolis", Appl Microbiol Biotechnol (1984) 20:378–383, by Kurane et al.

"Preparation and Properties of a Cephalosporin Acetylesterase Adsorbed onto Bentonite", Antimicrobial Agents and Chemotherapy, Sep. 1975, pp. 282–288.

"Purification and Properties of Esterase from Bacillus stearothermophilus", Archives of Biochemistry and Biophysics 160, 504–513 (1974), by Matsunaga et al.

"Effects of Carrier Morphology and Buffer Diffusion on the Expression of Enzymatic Activity", Biochimica et Biophysica Acta, 485 (1977) 367–378, by Konecny et al.

"Characterization of Intracellular Esterase A from Bacillus subtilis", Biochimica et Biophysica Acta, 429 (1976) 191–197, by Riefler III et al.

"Nucleotide sequence of the gene ereA encoding the erythromycin esterase in Escherichia coli, Gene, 35 (1985) 271–278, by Ounissi et al.

"An Esterase on the Outer Membrane of Pseudomonas aeruginosa for the Hydrolysis of Long Chain Acyl Esters", J. Biochem. 86, 643–656 (1979), by Ohkawa et al.

"Purification and Some Properties of Intracellular Esterase from Pseudomonas fluorescens", J. Biochem. 95, 1047–1054 (1984), by Nakagawa et al.

"Purification and Properties of Undecyl Acetate Esterase from Pseudomonas cepacia Grown on 2-Tridecanone", Journal of Bacteriology, Jun. 1974, pp. 880–889, by Shum et al.

"Mycobacteriocins Produced by Rapidly Growing Mycobacteria are Tween-Hydrolyzing Esterases", Journal of Bacteriology, Mar. 1983, pp. 1294–1300, by Saito et al.

"Identification and Localization of Two Membrane-Bound Esterases from Escherichia coli", Journal of Bacteriology, Jan. 1982, pp. 6–14, by Pacaud.

"Purification and Characterization of the Tween-Hydrolyzing Esterase of Mycobacterium smegmatis", Journal of Bacteriology, Sep. 1983, pp. 1249–1259, by Tomioka.

"Exocellular Esterase and Emulsan Release from the Cell Surface of Acinetobacter calcoaceticus", Journal of Bacteriology, Mar. 1985, pp. 1176–1181, by Shabtai et al.

"Distinctive Electrophoretic and Isoelectric Focusing Patterns of Esterases from Yersinia enterocolitica and Yersina pseudotuberculosis", Journal of General Microbiology (1984), 130, 1471–1480, by Goullet et al.

"Physiochemical Characterization of Tween 80-Hydrolyzing Esterases Produced by Rapidly Growing Mycobacteria", Microbiol. Immunol. vol. 27 (8), 673–681, 1983, by Tomioka et al.

NOVEL MICROORGANISM, A NOVEL ESTERASE AND METHOD FOR PREPARING THE SAME

The present invention relates to a novel microorganism, a novel esterase derived from a microorganism and a method for preparing the same. More particularly, the present invention relates to a novel microorganism belonging to genus Bacillus, a novel esterase obtainable by culturing a microorganism belonging to genus Bacillus and a method for preparing the same.

The word "esterase" is given to enzymes which are able to catalyze hydrolysis of substrates having ester bonds. It is classified by its substrate specificity into four, i.e., that to act on carboxylic acid ester, that to act on thiol ester, that to act on phosphoric acid ester, and that to act on sulfuric acid ester. In a narrow sense, "esterase" means only enzyme which is able to hydrolyze ester of lower fatty acid and is separated from "lipase" which is able to hydrolyze glycerol ester, among enzymes which act on carboxylic acid ester. Crude lipase has an esterase activity besides lipase activity, and these two activities are practically distinguished by the differences in heat resistance, sensitivity to trypsin and alkali, substrate specificity, i.e., chain length of fatty acid moiety of ester, etc.

However, the difference in the two activities is rather attributed to physical difference of existence condition of the substrate in the reaction mixture. That is to say, it is considered that the esterase reaction is performed by the reaction of enzyme with a substrate in aqueous solution but the lipase reaction proceeds at the interface between water and a substrate insoluble in water. [Sarda et al., Biochem. Biophys. Acta. 30 513 (1958)]. The esterase referred to in the present invention denotes that in the narrow sense as described above.

In recent years, there are extensive attempts to apply enzymes to organic synthesis, including hydrolysis of various ester compounds by use of an esterase to obtain optically active compounds or to create chiral compounds from prochiral compounds. Most of those reports relate to the use of pig liver esterase or porcine live esterate [, for example, Laumen et al., Tetrahedron Lett. 26 407–410 (1985); Schneider et al., Angew. Chem. Int. Ed. Engl. 23: 64–66 (1984); and Wang et al., J. Am. Chem. Soc. 106 3695 (1984)]. These methods are not economically practicable, because the pig liver esterase is expensive and hardly available in the market. Methods of using a microorganism which produces esterase instead of the pig liver esterase are also proposed, but there have been very few reports in which the purification and characterization of the esterase from the above microorganism are described [for example, Kotani, et al., Agric. Biol. Chem. 47 1363–1365 (1983); Fujimoto et al., J. Chem. Soc. Chem. Commun. 1333–1334 (1985); Brannon et al., J. Antibiot. 29 121–124 (1976); and Japanese Patent Publication (Kokai) No. 244295/1985].

It is reported that esterases are purified and characterized from the following microorganisms: (1) *Bacillus subtilis* ATCC 6633 [Biochem. Biophys. Acta. 485 367–378 (1977)]; (2) *Bacillus subtilis* SR22 [Biochem. Biophys. Acta. 429 191–197 (1976)]; (3) *Bacillus subtilis* NRRL-B-558 [Appl. Microbiol. 30 413–419 (1975)]; (4) *Bacillus stearothermophilus* [Archiv. Biochem. Biophys. 160 504–513 (1974)]; (5) *Pseudomonas aeruginosa* [J. Biochem. 86 643–656 (1979)]; (6) *Pseudomonas cepacia* [J. Bacteriol. 118 880–889 (1974)]; (7) *Pseudomonas fluorescens* [J. Biochem. 95 1047–1054 (1984) and Japanese Patent Publication (Kokai) No. 30681/1985]; (8) *Escherichia coli* K-12 [J. Bacteriol. 149 6–14 (1982)]; (9) *Aspergillus niger* NRRL337 [Agric. Biol. Chem. 47 1865–1868 (1983)]; and (10) *Mycobacterium smegmatis* ATCC 14468 [J. Baceteriol. 155 1249–1259 (1983)]. None of these reports refer at all to application to organic synthesis reaction, except application of esterase from *B. subtilis* NRRL-B-558 to synthesis of a cephalosporin derivative.

After having extensively looked for microbial esterases capable of being widely used in organic synthesis reactions, the present inventors found such an esterase produced from a novel microorganism, Bacillus sp. DC-1 (FERM BP-1254 Japanese Patent Application No. 92595/1986). The organism was isolated from soli, and possesses such properties as mentioned above. The present invention is based on this finding.

According to the present invention, a novel microbial esterase is provided, and an organic synthesis utilizing the novel microbial esterase. The economical production of optically active compounds and creation of chiral compounds from prochiral compounds is accomplished with the organic synthesis provided.

PHYSICOCHEMICAL PROPERTIES OF THE PRESENT ESTERASE (1) Activity:

Hydrolyze the ester bond of organic carboxylic acid ester.

(2) Substrate specificity:

Active mainly to an alcohol ester of organic carboxylic acid and highly active to water-soluble short chain fatty acid ester. Active to short chain mono- and tri-acyl glycerides but not to long chain mono-, di-, and tri-acyl glycerides. Active to palmitoyl-CoA but not to acetyl-CoA, choline ester and cholesterol ester.

(3) Optimum pH and pH stability:

The optimum pH for hydrolysis in the case of using p-nitrophenyl ester of 2,2-dimethyl-3-(2,2-dichlorovinyl)cyclopropane carboxylic acid (the acid itself being hereinafter referred to as DCPI) of the formula (I) as a substrate is 8.5–9.0.

(I)

when 10 mM Tris-hydrochloric acid buffer solution (pH 7.0–9.0) and 10 mM phosphate buffer solution (pH 5.0–7.0) are used, remaining activities after having treated in said buffer solution for 48 hours at 4° C., pH 7.0–9.0 6.0 and 5.0 are about 100%, about 45%, and about 20%, respectively.

(4) Optimum temperature and heat stability:

The optimum temperature for hydrolysis in the case of using p-nitrophenyl ester of DCPI as a substrate in 100 mM Tris-HCl buffer (pH 9.0) 50°–55° C.

Remaining activities after having treated in said buffer solution for 10 minutes at 35° C., 40° C. and 50° C. are 100%, about 80%, and about 15%, respectively.

(5) Molecular weight:

54,000±2,000 (by gel filtration and SDS-polyacrylamide gel electrophoresis)

(6) Isoelectric point:

4.8±0.1

(7) Inactivation conditions:

(a) Completely inactivated by treatment with 100 μM phenylmethylsulfonylfluoride (PMSF) or 80 μM diisopropyl fluorophosphate (DIFP) at 37° C. for 10 minutes.

(b) The activity decreases about 25% and about 70% by treatment with 100 mM Tris-HCl buffer solution (pH 9.0) containing 1 mM sodium deoxycholate and 5 mM sodium lauryl sulfate, respectively, at 37° C. for 10 minutes.

The esterase of the present invention is a single chain peptide having no sub-unit structure and has a molecular weight of 54,000±2,000. This is distinguished from any of esterases derived from *Bacillus subtilis* ATCC 6633 (150,000), *Bacillus subtilis* NRRL-B-558 (190,000), *Bacillus subtilis* SR-22 (160,000), *Bacillus stearothermophilus* (42,000–47,000), *Pseudomonas capacia* (34,500), *Pseudomonas fluorescens* (48,000), *Aspergillus niger* NRRL 337 (23,000, 27,800, 29,500, 127,000) and *Mycobacterium smegmatis* ATCC 14468 (36,000–41,000) in these points. Furthermore, although the esterase from *Pseudomonas aeruginosa* is not inactivated by treatment with diisopropyl fluorophosphate or sodium lauryl sulfate, the esterase of the present invention is inactivated about 70% by treatment with 5 mM sodium lauryl sulfate and 100% with 80 μM diisopropyl fluorophosphate. Further, the esterase from *Escherichia coli* K-12 is to be termed as a membrane-bound carboxyl peptidase, but the esterase of the present invention is localized in the cytoplasm.

Thus, the esterase according to the present invention is a novel esterase which has heretofore never been known.

A PROCESS FOR PRODUCING THE ESTERASE

The process comprises culturing a microorganism belonging to the genus Bacillus and having a capacity to produce the novel esterase above-mentioned until said enzyme is accumulated in bacterial cells thereof, separating the cells and recovering the esterase therefrom.

The esterase of the present invention is produced by the use of a microorganism. Any bacteria may be used as long as they belong to the genus Bacillus and have ability to produce the enzyme aforementioned. One of bacteria is Bacillus sp. DC-1 which is deposited at Fermentation Research Institute, Industrial Technology Agency, Japan, under the deposition No. FERM BP-1254 (it was transfered from the deposition No. FERM P-8719).

TAXONOMICAL CHARACTERISTICS OF BACILLUS SP. DC-1

(a) Morphological characteristics
(1) Form and size of cell:
 Rods, (0.5–0.6) μm×(1.2–1.7) μm. occuring singly or in short chains.
(2) Polymorphism: None
(3) Motility: Mobile by peritrichous flagella.
(4) Spore formation: Endospores formed. Spherical or slightly oval with 0.4–0.6 μm in diameter. Spores formed in a terminal position of the vegetative cell, having swell.
(5) Gram staining: Negative
(6) Acid fastness: Negative
(b) Cultural characteristics
(1) Nutrient agar plate (35° C., 24 hours)
 Shape: Circular and projected form
 Surface: Smooth and lustrous
 Color tone: Translucent and yellowish white
(2) Nutrient agar slant (35° C., 24 hours)
 Growth degree: Moderate, growing like spread cloth or beads-like
 Surface: Smooth and lustrous
 Color tone: Translucent and yellowish white
(3) Nutrient broth (35° C., 24 hours)
 Growth degree: Moderate
 Coloring/discoloring: None
 Pellicle: Not formed
 Sediment: Formed
(4) Gelatine stab (35° C., 14 days)
 No liquefaction.
(5) Litmus milk (35° C., 14 days)
 Slightly alkaline. No coagulation nor peptonization.
(c) Biochemical characteristics:
Cultured at 35° C. for 1–5 days. Negative ones were observed up to 14 days.
(1) Reduction of nitrate: Positive Nitrite produced from nitrate.
(2) Denitrification: Negative
(3) MR test: Negative
(4) VP test: Negative
(5) Production of indole: Negative
(6) Production of hydrogen sulfide: Negative
(7) Hydrolysis of starch: Negative
(8) Utilization of citric acid:
 Koser medium: Negative
 Christensen medium: Positive
(9) Utilization of inorganic nitrogen sources:
 Modified method of Stanier et al.'s medium by Yamazato et al.: (Yamazato et al. J. Gen. Appl. Microbiol. (1982) 28: 195–213)
 Sodium succinate was used as the sole carbon source.
 Nitrate: Not utilized.
 Ammonium salt: Utilized.
(10) Pigmentation: Negative
(11) Urease:
 Christensen urea medium: Positive
(12) Oxidase: Positive
(13) Catalase: Positive
(14) Range of growth:
 Growth temperature: 10°–45° C. (optimum 30°–35° C.)
 Growth pH: 6.0–9.5 (optimum 8.5–9.0)
(15) Anaerobic or aerobic growth: Aerobic
(16) OF test: Negative
(17) Production of acid or gas from saccharides:

| | Acid | Gas |
|---|---|---|
| (1) L-arabinose | — | — |
| (2) D-xylose | — | — |
| (3) D-glucose | — | — |
| (4) D-mannose | — | — |
| (5) D-fructose | — | — |
| (6) D-galactose | — | — |
| (7) Maltose | — | — |
| (8) Sucrose | — | — |
| (9) Lactose | — | — |
| (10) Trehalose | — | — |
| (11) D-sorbitol | — | — |
| (12) D-mannitol | — | — |
| (13) Inositol | — | — |
| (14) Glycerin | — | — |
| (15) Starch | — | — |

Reference is made to Bergey's Manual of Determinative Bacteriology, 8th Ed (1974). The strain is identified as that belonging to genus Bacillus, since it is able to grow under aerobic conditions and forms endospores. The present strain is close to but different from *Bacillus sphaericus* and *Bacillus pasteurii*, as shown in the table below:

|  | the Present strain | Bacillus sphaericus | Bacillus pasteurii |
|---|---|---|---|
| Reduction of nitrate | + | − | − |
| Requisition of urea or ammonia | − | − | + |

In view of the above facts, the present inventors have recognized the strain to be a novel one belonging to genus Bacillus and nominated it Bacillus sp. DC-1. This strain was deposited with Fermentation Research Institute, Industrial Technology Agency, Japan, under FERM BP-1254.

Mutants derived by induced mutation by an ordinary mutation inducing process such as physical treatment e.g., irradiation of ultra-violet ray, x-ray, gamma-ray, etc. or chemical treatment with nitrosoguanidine or the like or by natural mutation attributed to natural cause from the above strain, are within the scope of the present invention. Any strain belonging to genus Bacillus and producing above mentioned novel esterase are also within the scope of the present invention.

Isolation of the present strain from soil was carried out by usual manner familiar to the skilled in the art, using a culturing medium containing the ethyl ester of DCPI as the sole carbon source.

Culturing of the strain isolated is effected in any synthetic or natural culturing medium, provided that it contains suitable amounts of assimilable carbon sources, nitrogen sources, inorganic substances and other nutritives. A liquid or solid culturing medium may be used. Examples of the carbon sources include saccharides such as glucose, fructose, maltose, galactose, ribose, succharose, starch, starch hydrolyzate, molasses, waste molasses, etc.; natural carbohydrates such as wheat, rice, etc.; alcohols such as glycerol, mannitol, methanol, ethanol, etc.; fatty acids such as gluconic acid, piruvic acid, acetic acid, citric acid, etc.; hydrocarbons such as normal paraffin, kerosine, etc.; amino acids such as glycine, glutamic acid, glutamine, alanine, asparagin, etc. One or more of the above carbon sources may be used depending on assimilability of the strain to be cultured.

Examples of the nitrogen sources include organic nitrogen compounds such as meat extract, peptone, yeast extract, dry yeast, soybean hydrolyzate, soybean powder, milk casein, Casamino acid, various amino acids, corn steep liquor, fish meal or hydrolyzate thereof, other hydrolyzates of animals, vegetables and microorganisms, and inorganic nitrogen compounds such as ammonium salts, e.g., ammonia, ammonium nitrate, ammonium sulfate, ammonium chloride, ammonium phosphate, ammonium acetate, etc., and nitrate, e.g. sodium nitrate, urea, etc. One or more of these compounds may be used depending upon assimilability of the strain to be cultured.

As inorganic salt, a suitable amount of one or more of phosphate, chloride, sulfate, carbonate, acetate, etc. of magnesium, manganese, iron, zinc, copper, sodium, calcium, potassium, etc. may be added. If necessary, a defoaming agent such as vegetable oil, a surface active agent, etc. may be added.

Cultivation can be carried out in the usual procedure such as shaking culture, aeration stirring culture, static culture, continuous culture, etc., when the cultivation is effected in liquid culturing medium containing the above components.

The culturing conditions are not so critical that any conditions may be suitably selected depending on culturing medium and culturing method to be employed, as long as the present strain grows to produce esterase. Preferred is to control the starting pH at 8–9 and incubate under the temperature of 30°–35° C. Incubation is effected usually for 1–2 days.

Recovery or extraction of esterase which has been accumulated in bacterial cells is effected by the following procedures:

After incubation is over, the bacterial cells are harvested by techniques such as filteration or centrifugation, washed with water or buffer solution, and then subjected to breakup. To this breakup, any of the following is applied singly or combined: physical techniques such as freezing and thawing, ultrasonic treatment, pressurization treatment, osmotic pressure difference treatment, grinding, air-drying using acetone, etc., a biochemical treatment such as cell wall dissolution enzyme treatment using lysozyme, cellulase, or a chemical treatment such as treatment in contact with a surface active agent, etc.

An example of such process is given, as follows:

Bacterial cells are harvested by centrifugation, washed several times with 100 mM potassium phosphate buffer (pH 9.0), and resuspended in the same buffer. The cells are broken by a French Press at a pressure, to extract esterase. The crude esterase extracted from the bacterial cells is purified by single or combined use of the per se conventional means in the field of the biochemistry such as salting out, fractional precipitation by organic solvents, column chromatography such as ion exchange chromatography, gel filtration chromatography, hydrophobic chromatography, hydrogen bond chromatography, affinity chromatography, etc., or high performance liquid chromatography or electrophoresis.

An example of the purification procedure is given below:

The cells are broken by a French Press and the cell debris are removed by centrifugation at 10,000×g for 10 minutes. The supernatant is subjected to ultra-centrifugation at 100,000×g for 60 minutes and the resulting supernatant is used as a crude extract.

The esterase is precipitated with 40–70% saturation of ammonium sulfate and the precipitate is dissolved with 20 mM Tris-HCl buffer (pH 7.0). The resulting solution is dialized against the same buffer, and passed through DEAE-Sepharose CL-6B equilibrated with the same buffer to adsorb the esterase. Then, the esterase is eluted with a linear concentration gradient with 0–0.5M NaCl. The fraction having esterase activity which is eluted in the vicinity of 0.25M NaCl is concentrated, and then dialyzed against 50 mM Tris-HCl buffer (pH 8.0). The resulting concentrate is passed through Sephacryl S-200 Super-fine equilibrated with the same buffer, and the eluted esterase fraction is concentrated, and then passed through Sephadex G-150 Super-fine column equilibrated with the same buffer to elute esterase. After the resulting esterase fraction is concentrated, it is dialyzed against 20 mM Tris-HCl buffer (pH 8.0), and passed through QAE-Sephadex equilibrated with the same buffer to adsorb esterase, and then the esterase is eluted with 0–0.5M NaCl linear concentration gradient.

After concentration, the eluate was subjected to SDS-polyacrylamide gel electrophoresis to find that the present esterase is purified in a single band on electrophoresis and has a molecular weight of 54,000, and is a single chain peptide having no subunit structure.

An example is given in the following Table to show the above purification process.

| Purification Process | Total Activity (Units) | (Yield) (%) | Total Protein (mg) | Specific Activity (Units/mg) | Purification (fold) |
|---|---|---|---|---|---|
| 1. Crude extract | 7498 | (100) | 1536.6 | 4.86 | (1.0) |
| 2. (NH$_4$)$_2$SO$_4$ 40–70% | 4199 | (56.0) | 614.6 | 6.80 | (1.4) |
| 3. DEAE-Sepharose CL-6B | 3734 | (49.8) | 66.6 | 56.0 | (11.5) |
| 4. Sephacryl S-200 | 3612 | (48.2) | 19.9 | 181.5 | (37.2) |
| 5. Sephadex G-150 | 2287 | (30.5) | 10.5 | 217.8 | (44.8) |
| 6. QAE-Sephadex | 745 | (9.9) | 1.8 | 413.8 | (84.7) |

ENZYME ASSAY

An esterase solution is added to 100 mM Tris-HCl buffer of pH 9.0 and the mixture is preincubated at 40° C. for 1 minute. Then p-nitrophenyl ester of DCPI of the following formula (I) dissolved in acetone is added so as to make the final concentration 1 mM, and the mixture is stirred, after which the increase of absorbance at 405 nm resulting from liberation of p-nitrophenol is determined with a spectrophotometer. One unit of estrase is defined as the amount of enzyme which liberates 1 nmole p-nitrophenol per minute.

Then, the present invention is illustrated by way of examples. It is to be noted however that the scope of the present invention is not in any way limited by them.

EXAMPLE 1

(Isolation of strain)

A small spoonful (about 0.5 g) of soil collected in Takarazuka City, Hyogo Prefecture, Japan, was added to 10 ml of a medium having ethyl ester of DCPI as the sole carbon source as in the table below and the mixture was incubated with shaking at 30° C. for 3 days. The culture (0.1 ml) was inoculated into a fresh medium described above and similarly incubated.

Composition of Culturing Medium

Ethyl ester of DCPI: 60 mg
KH$_2$PO$_4$: 0.5 g
K$_2$HPO$_4$: 0.5 g
(NH$_4$)$_2$SO$_4$: 2.0 g
Yeast extract: 1.0 g
MgSO$_4$.7H$_2$O: 0.2 g
CuSO$_4$.5H$_2$O: 5 mg
MnCl$_2$.4H$_2$O: 5 mg
ZnSO$_4$.7H$_2$O: 1 mg
FeSO$_4$.7H$_2$O: 2 mg
Distilled water: 1 liter
pH 9.0 (adjusted with 10% Na$_2$CO$_3$)

After the above operation was repeated three times, the cultures in which proliferation was recognized were diluted to an appropriate concentration with sterilized water. The diluted solution was smeared on an agar plate made by adding agar to a medium described above to 2% concentration and incubated at 30° C. for 4 days. Transplantation to a fresh agar plate described above was repeated until it was possible to confirm by eye and microscopically that the produced plural colonies were not different from one another. The present strain Bacillus sp. DC-1 (FERM BP-1254) was thus obtained.

The growth condition and physiological properties of the strain in various mediums are as stated hereinabove.

EXAMPLE 2

A loopful of cells of Bacillus sp. DC-1 (FERM BP-1254) was inoculated in 50 ml of a medium (soluble starch 1%, polypeptone 0.5%, yeast extract 0.5%, K$_2$HPO$_4$ 0.1%, MgSO$_4$.7H$_2$O 0.02%, CuSO$_4$.5H$_2$O 5 mg/l, MnCl$_2$.4H$_2$O 5 mg/l, ZnSO$_4$.7H$_2$O 1 mg/l, FeSO$_4$.7H$_2$O 2 mg/l, pH 9.0). Cultivation was carried out with shaking at 30° C. for 24 hours. Seed culture was inoculated into 5 liters of a fresh medium described above and incubated at 35° C. for 24 hours at aeration rate of 5 liters/min. at the stirring rate of 600 rpm. After the cultivation was over, bacterial cells were harvested by centrifugation at 9,000×g for 10 minutes and washed twice with 100 mM potassium phosphate buffer (pH 9.0). The cells corresponding to 100 ml of the culture were suspended in 4 ml of the same buffer, and then broken with a French Pressure Cell Press (made by Aminco) at 4° C. under pressure of 38,000 psi.

The resulting bacterial cells thus treated was centrifuged (10,000×g, 10 minutes), followed by subjecting the supernatant thereof to ultracentrifugation (100,000×g, 60 minutes) to obtain a crude extract of esterase. As a result, there was obtained 6,560 mg of crude enzyme having specific activity of 4.86 units/mg.

EXAMPLE 3

The crude esterase extract obtained in accordance with Example 2 was adjusted with 100 mM potassium phosphate buffer (pH 9.0) to protein concentration of 10–20 mg/ml. Ammonium sulfate was added to the solution to 40% saturation and the precipitate was removed by centrifugation (10,000×g, 10 minutes). Ammonium sulfate was added to the supernatant to 70% saturation and the precipitate was harvested by centrifugation (10,000×g, 10 minutes). The precipitate was dissolved in 40 ml of 20 mM Tris-HCl buffer (pH 7.0), and dialyzed against the same buffer solution. As a result, there was obtained a crude enzyme solution (43.5 ml) having the total activity of 17848 units and the specific activity of 6.80 units/mg.

A part of the resulting esterase solution (10.2 ml, 4199 units, 615 mg prot.) was passed through DEAE-Sepharose CL-6B (2.6×26 cm) having bed volume of 140 ml equilibrated with the same buffer to adsorb the esterase to DEAE-Sepharose CL-6B, after which the column was washed with the same buffer solution, and the esterase was eluted in the vicinity of 0.25M NaCl with a linear concentration gradient with 0–0.5M NaCl. As a result, the activity was recovered by 3734 units (89%) in the peak portion, or by 4,115 units (98%) in the total eluate, and the specific activity showed a rise by 8.2 times.

The esterase active fraction was concentrated through an ultrafiltration membrane, dialyzed against 50 mM Tris-HCl buffer (pH 8.0), and passed through Sephacryl S-200 Superfine (2.6×100 cm) equilibrated with the same buffer solution to effect gel filtration. The eluted esterase fraction was concentrated and passed through Sephadex G-150 Superfine column (2.6×100 cm) equilibrated with 50 mM Tris-HCl buffer (pH 8.0) to elute the esterase with the same buffer. The resulting esterase fraction was concentrated and passed through QAE-Sephadex column (1.6×35 cm, bed volume 70 ml) equilibrated with 20 mM Tris-HCl buffer (pH 8.0), followed by washing with the same buffer. The esterase was eluted with a linear concentration gradient with 0–0.5M NaCl to recover the esterase of 745 unit activity in the portion of NaCl 0.5–0.3M; the specific activity was 413.8 units/mg; and the activity recovery yield from the crude extract was 9.9%.

The resulting esterase solution was concentrated to about 5-fold concentration, and then subjected to 10% SDS-polyacrylamide gel electrophoresis, whereupon the esterase was noticed as a single band of molecular weight 54,000. It showed good identity with the results of gel filtrations with Sephacryl S-200 Superfine and Sephadex G-150 Superfine (52,000–58,000), and suggested that the esterase is a single chain peptide having no sub-unit structure. In this assay, Phosphorylase B (molecular weight 92,500), bovine serum albumin (66,200), egg albumin (45,000), carbonic anhydrase (31,000), soybean trypsin inhibitor (21,500) and lysozyme (14,400) were used as the standard substances for determining the molecular weight of the esterase by SDS-PAGE, and blue dextran (200,000), bovine serum albumin (66,200), egg albumin (45,000), chymotrypsinogen A (25,000), and ribonuclease A (13,700) were used as the standard substances for determining the molecular weight of the esterase by gel filtration.

EXAMPLE 4

The purified esterase obtained in accordance with Example 3 was subjected to an isoelectric electrophoresis (constant power: 15 W) in the range of pH 4.0–6.5 using polyacrylamide gel (concentration 5%, crosslinking degree 3%, Ampholine concentration 2.2%; LKB) at 10° C. for 90 minutes. After the electrophoresis, protein was detected by staining with Coomassie brilliant blue R-250. As a result, the isoelectric point of the present esterase was 4.8±0.1. As the standard substances in the electrophoresis, there were used PI marker (PI 4.65, 5.10, 6.00, 6.50; Bio Rad) and PI marker (PI 4.10, 4.90, 6.40; Oriental Yeast).

EXAMPLE 5

The purified esterase obtained in accordance with Example 3 was incubated at 37° C. for 10 minutes together with the reagents described below, and the remaining enzyme activity was assayed in accordance with the aforementioned assay method. The results are expressed in the following Table. In Table, the remaining activity is expressed in relative value (%) based on untreated activity taken as 100.

| Additive | Concentration | Remaining activity(%) |
|---|---|---|
| — | — | 100.0 |
| Tritonx-100 | 5% | 101.5 |
| Tween-80 | 5% | 130.8 |
| Sodium deoxycholate | 0.1 mM | 76.2 |
| Sodium lauryl sulfate | 5.0 mM | 32.2 |
| PMSF* | 80 μM | 1.5 |
| DIFP** | 90 μM | 0 |

*phenylmethylsulfonylfluoride
**diisopropyl fluorophosphate

EXAMPLE 6

The purified esterase obtained in accordance with Example 3 was applied to each substrate (2–20 mM) in 100 mM Tris-HCl buffer (pH 9.0) and its hydrolysis activity was observed with a pH-stat (made by Radiometer). Also, the hydrolysis activities of the present esterase to choline ester, cholesterol ester, and thiol ester were determined. The results are shown in Tables 1 and 2.

In Table 1, the hydrolysis activity is expressed in relative activity (%) based on the hydrolysis activity of the present esterase to ethyl butyrate taken as 100. Each substrate was used after it was emulsified with 0.2% polyvinyl alcohol. In Table 2, hydrolysis activities to choline ester and cholesterol ester were observed by the use of the Cholinesterase B-test (Wako) and Free-Cholesterol B-test (Wako), respectively, and hydrolysis activity to thiol ester was based on increase in absorbance at 412 nm with a spectrophotometer in which glutathione, a standard substance, and 5,5'-dithiobis(2-nitrobenzoic acid) (DTNB) were employed. The activity is expressed in mole numbers of choline, cholesterol, and CoA to be liberated per minute.

TABLE 1

| Substrate | Concentration (mM) | Relative activity (%) |
|---|---|---|
| Ethyl butyrate | 20 | 100.0 |
| Isopropyl palmitate | 20 | 1.7 |
| 1-palmitoyl glycerol | 5 | 3.0 |
| 1,2-dipalmitoyl glycerol | 5 | 0.2 |
| 1,3-dipalmitoyl glycerol | 2 | 0 |
| Triacetin | 20 | 14.1 |
| Tributylin | 20 | 56.6 |
| Tripalmitin | 6 | 1.1 |

TABLE 2

| Substrate | Concentration (μM) | Activity (nmol/min) |
|---|---|---|
| Acetyl choline | 100 | 0 |
| Benzoyl choline | 100 | 0 |
| Cholesterol acetate | 1,300 | 0 |
| Cholesterol linolate | 1,300 | 0 |
| Acetyl CoA | 50 | 0 |
| Palmitoyl CoA | 50 | 5.4 |

EXAMPLE 7.

The optimum pH and pH stability range of the purified esterase obtained in accordance with Example 3 were measured when a substrate was p-nitrophenyl ester of DCPI. The results are shown in FIG. 1 and FIG. 2.

Figure 1:
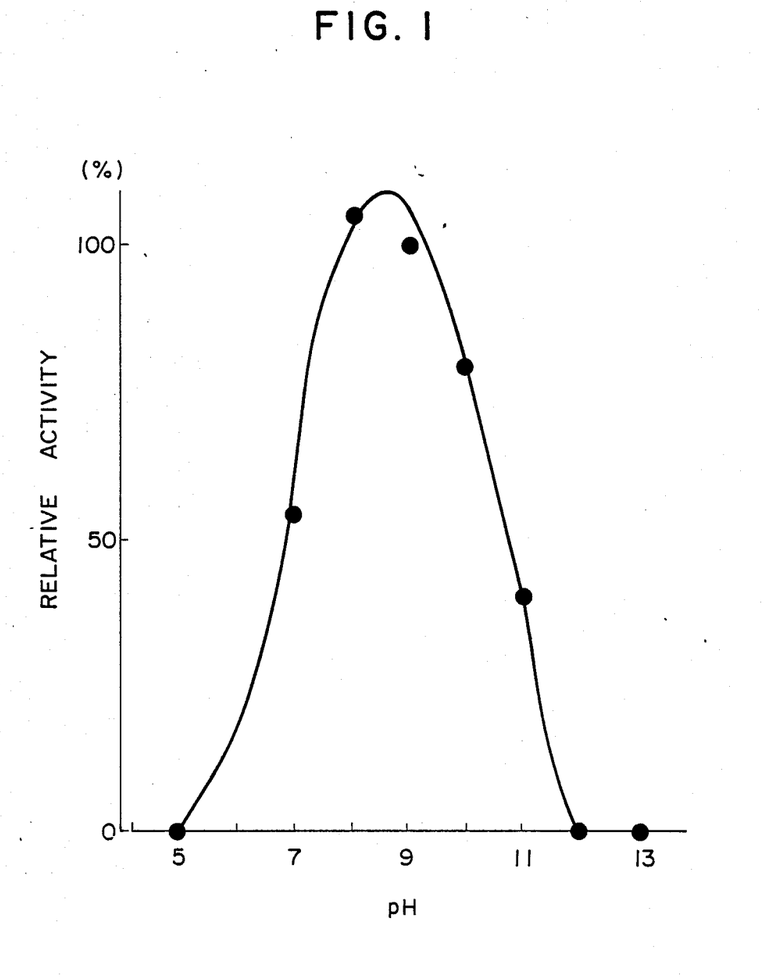

In FIG. 1, the test was effected at 40° C., wherein 100 mM potassium phosphate buffer was used for pH 5–7, 100 mM Tris-HCl buffer for pH 7–9, and 100 mM dipotassium phosphate-potassium hydroxide buffer for pH 9–13, respectively. The activity was expressed in relative activity (%) based on the activity value at pH 9.0 taken as 100.

Figure 2:
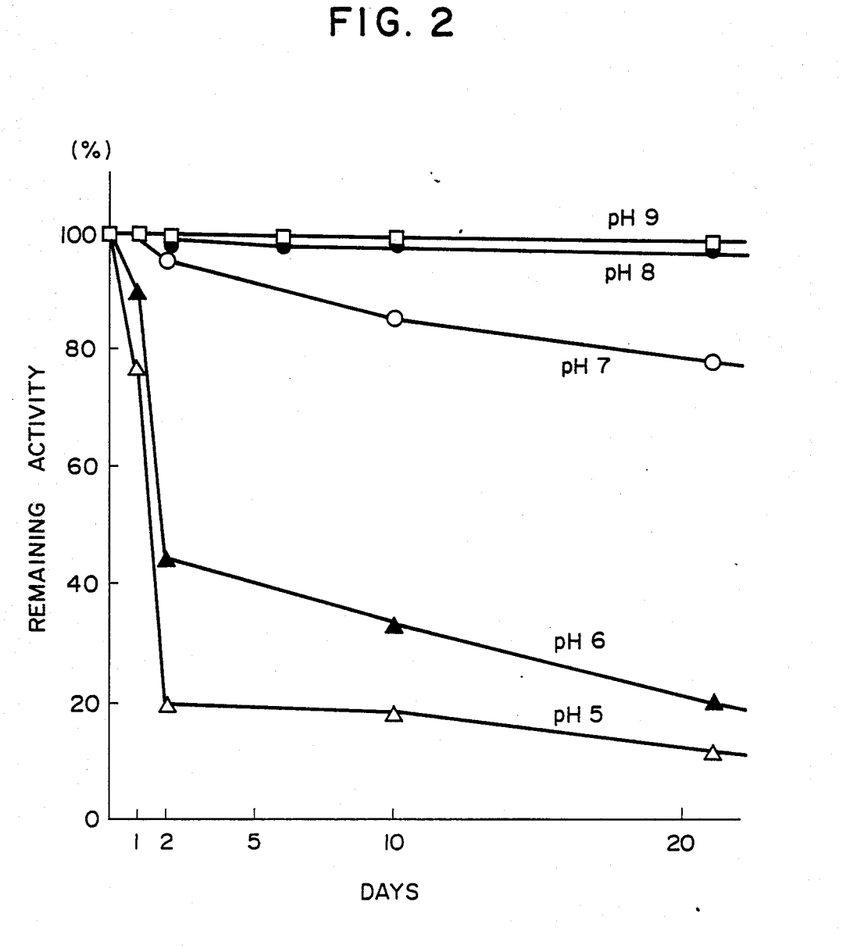

In FIG. 2, the enzyme solution was preserved at 4° C. in 20 mM potassium phosphate buffer for pH 5–7, and in 20 mM Tris-HCl buffer for pH 7–9, respectively, and the remaining activity in each time was measured in 100 mM Tris-HCl of pH 9.0 at 40° C. The activity is expressed in remaining activity rate (%) based on the activity value in 0 hour taken as 100.

EXAMPLE 8

Figure 3:
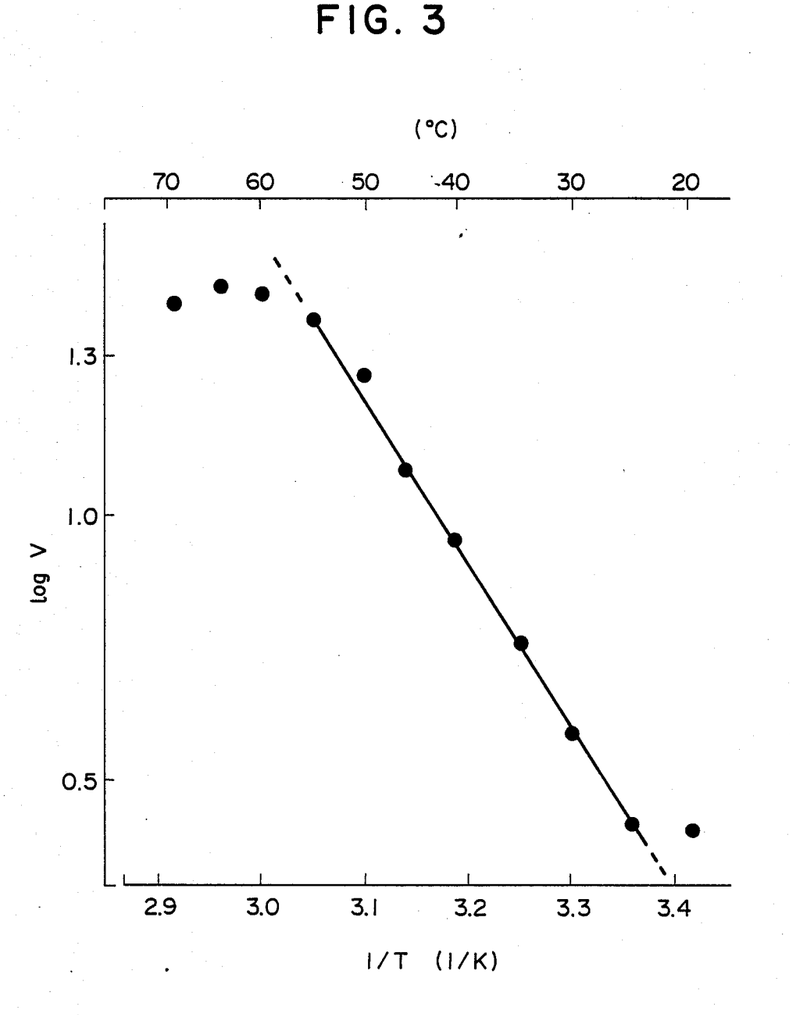
Figure 4:
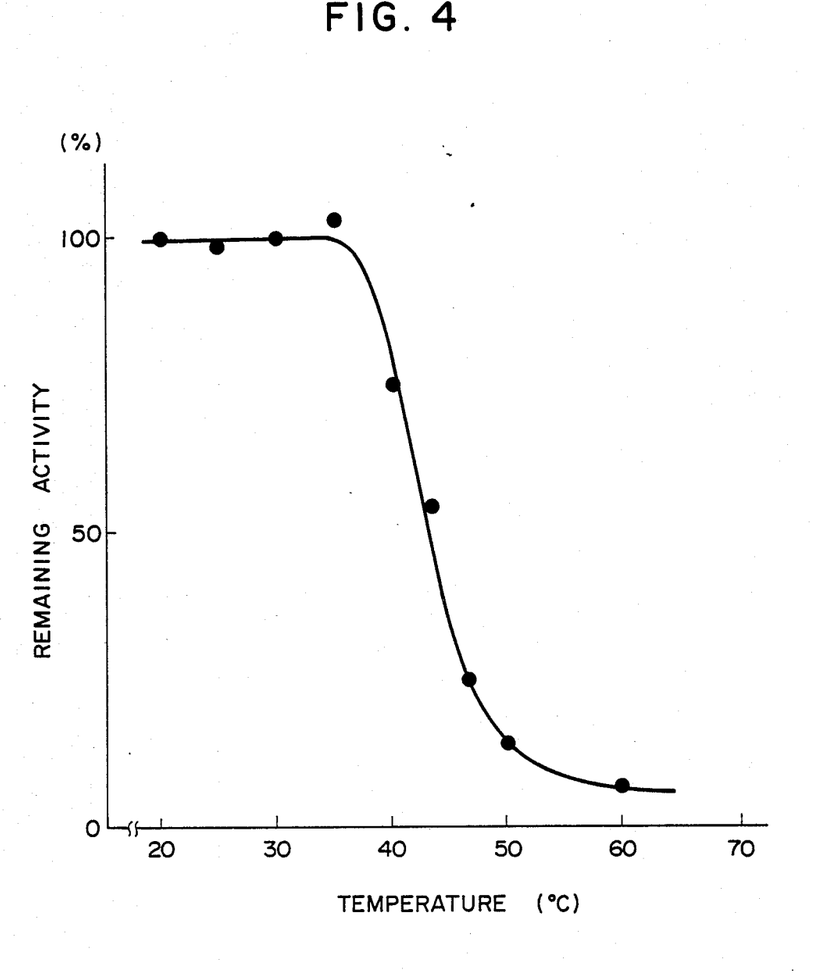

The optimum temperature and heat stability of the purified esterase obtained in accordance with Example 3 were determined. Results are shown in FIG. 3 and FIG. 4. In FIG. 3, the axis of abscissas shows reciprocal of the absolute temperature, and the axis of ordinate shows logarithm of initial velocity. Activities were measured by the use of 100 mM Tris-HCl buffer of pH 9.0.

In FIG. 4, the enzyme solution was pretreated for 15 minutes at each temperature shown on abscissa, after which activity was measured in 100 mM Tris-HCl buffer (pH 9.0) at 40° C. Activity is shown in remaining activity rate (%) based on activity of the untreated esterase taken as 100.

REFERENCE EXAMPLE 1

Ethyl ester of DCPI (DCPE) was subjected to hydrolysis reaction as follows wherein the crude esterase solution obtained in accordance with the ammonium sulfate precipitation method as described in Example 3 (ammonium sulfate 40–70% saturation fraction, specific activity 6.80 units/mg) was used.

The above crude enzyme solution (1.0 ml) (410 units, 60.3 mg) was added to 100 mM Tris-HCl buffer (pH 9.0, 8.0 ml) containing 1.0 ml of 2% polyvinyl alcohol, and then, to the mixture was added (±)-cis, trans DCPE (cis/trans ratio=45/55) until the ultimate concentration of DCPE reached 2 mM. The mixture was allowed to react with stirring at 35° C. for 96 hours. After the reaction for 96 hours, 35% HCl (0.1 ml) was added to the reaction mixture to stop the reaction, and diethylether was added to the resulting mixture in order to extract DCPI and unaltered DCPE.

The extract was subjected to gas chromatography (column: 30% Thermon 3000, 1.1 m, 140° C.) and yield (%) was calculated from the peak area ratio of DCPI to DCPE.

Then, 1N NaOH (2.0 ml) was added to the above extract until DCPI only was extracted as a sodium salt in an aqueous layer. Then the aqueous layer was adjusted below pH 2 with 35% HCl, the separated DCPI was extracted with methyl isobutyl ketone and concentrated. DCPI obtained was dissolved in toluene (0.5 ml), to which thionyl chloride, pyridine, and 3,5-dichloroaniline of the equimolar amounts to DCPI were added, and the mixture was allowed to react at 80° C. to produce anilide. The resulting product was subjected to analysis of isomer by high performance liquid chromatography [column: SUMIPAX OA-2100, eluent: n-hexane-dichloroethane (10:3 v/v), flow rate: 1.0 ml/min.]. The results are shown in Table 3.

TABLE 3

| Yield* (%) | DCPI Isomer ratio (%) | | | |
|---|---|---|---|---|
| | (+)-trans | (−)-trans | (+)-cis | (−)-cis |
| 100 | 97.0 | 3.0 | 0 | 0 |

*mole yield of the obtained (+)-trans DCPI to the (+)-trans DCPE in the starting compound.

Asymmetric hydrolysis reaction of DCPE by utilizing the present strain is given in Reference Example 2.

REFERENCE EXAMPLE 2

A solution of yeast extract (5 g), polypeptone (5 g), potassium dihydrogen phosphate (1 g) and magnesium sulfate (septahydride) (0.2 g) in 1 liter of distilled water was adjusted to pH 9.0 with an aqueous solution of 10% sodium carbonate. This liquid medium (10 ml) was put into a test tube (24 mm in diameter), sterilized under steam in an autoclave at 120° C. for 15 minutes. A loopful of cells of Bacillus sp. DC-1 was inoculated thereto. Cultivation was carried out at 30° C. for 24 hours with shaking to make a seedculture.

The medium of the same composition as above (100 ml) in a 500-ml Erlenmeyer flask was similarly sterilized and 1 ml of the seedculture was inoculated thereto. Cultivation was carried out at 30° C. for 24 hours with shaking. Thereafter, 0.6 g of racemic DCPE (cis/trans ratio=45/55) was added to the culture, and incubated at 30° C. for 96 hours.

To the resulting reaction mixture was added 1 ml of 35% HCl and then DCPI and unaltered DCPE were extracted with 50 ml of methyl isobutyl ketone.

The extract was subjected to gas chromatography and yield was calculated as described in Reference Example 1.

To the above extract was added 20 ml of 1N NaOH and DCPI was extracted as described in Reference Example 1. The resulting DCPI (5 mg) was dissolved in 1 ml of toluene and thionyl chloride, pyridine, and dichloroaniline of the equimolar amounts to DCPI were added to produce anilide. Assay of isomers by high performance liquid chromatograph [column: SUMIPAX QA-21200, eluent: n-hexane-dichloroethane (17:3, v/v), flow rate: 1.0 ml/min.] gave the results shown in Table 4.

TABLE 4

| Yield* (%) | Isomer ratio of DCPI (%) | | | |
|---|---|---|---|---|
| | (+)-trans | (−)-trans | (+)cis | (−)cis |
| 100 | 90.1 | 9.9 | 0 | 0 |

*mole yield of the resulting (+)-trans-DCPI to the (+)-trans-DCPE contained in the starting compound

We claim:

1. A process for preparing a novel esterase having the following physicochemical properties, which process comprises cultivating the microorganism Bacillus sp. DC-1 (FERM BP-1254) which is capable of producing an esterase having the following physicochemical properties, and recovering said esterase from the cells;
    (1) Activity;

hydrolyzes the ester bond of organic carboxylic acid ester;

(2) Substrate specificity:
   active mainly to an alcohol ester moiety of organic carboxylic acid and highly active to water-soluble short chain fatty acid ester; active to short chain mono- or tri-acyl glycerides but not to long chain mono-, di- or tri-acyl glycerides; active to palmitoyl-CoA but not to acetyl-CoA, choline ester or cholesterol ester;

(3) Optimum pH and pH stability:
   optimum pH for hydrolysis in the case of using p-nitrophenyl ester of 2,2-dimethyl-3-(2,2-dichlorovinyl)-cyclopropane carboxylic acid of the formula (I) as a substrate is 8.5–9.0;

when 10 mM Tris-HCl buffer solution (pH 7.0–9.0) is used for hydrolysis of the above substrate at 4° C., remaining activity after 48 hours is about 100%; when 10 mM of phosphate buffer solution (pH 6.0) is used, the remaining activity is about 45%; and when 10 mM of phosphate buffer solution (pH 5.0) is used, the remaining activity is about 20%;

(4) Optimum temperature and heat stability:
   optimum temperature for hydrolysis in the case of using p-nitrophenyl ester of 2,2-dimethyl-3-(2,2-dichlorovinyl)-cyclopropane carboxylic acid as a substrate in 100 mM Tris-HCl buffer (pH 9.0) is 50°–55° C.;
   remaining activities after treating in 100 mM Tris-HCl buffer solution (pH 9.0) for 10 minutes at 35° C., is about 100%, at 40° C. about 80%, and at 50° C. about 15%;

(5) Molecular weight:
   54,000±2,000 (by gel filtration and SDS-polyacrylamide gel electrophoresis)

(6) Isoelectric point: 4.8±0.1

(7) Inactivating conditions:
   (a) completely inactivated by treatment with 100 μM phenylmethylsulfonyl fluoride or 80 μM diisopropyl fluorophosphate at 37° C. for 100 minutes;
   (b) activity decreased about 25% and about 70% by treatment with 100 mM Tris-HCl buffer solution (pH 9.0) containing 1 mM sodium deoxycholate and 5 mM sodium lauryl sulfate, respectively, at 37° C. for 10 minutes.

2. A biologically pure culture of Bacillus sp. DC-1 (FERM BP-1254) capable of producing recoverable amounts of an enzyme having the following physiochemical properties:

(1) Activity:
   hydrolyzes the ester bond of organic carboxylic acid ester;

(2) Substrate specificity:
   active mainly to an alcohol ester moiety of organic carboxylic acid and highly active to water-soluble short chain fatty acid ester; active to short chain mono- or tri-acyl glycerides but not to long chain mono-, di-, or tri-acyl glycerides; active to palmitoyl-CoA but not to acetyl-CoA, choline ester or cholesterol ester;

(3) Optimum pH and pH stability:
   optimum pH for hydrolysis in the case of using p-nitrophenyl ester of 2,2-dimethyl-3-(2,2-dichlorovinyl)cyclopropane carboxylic acid of the formula (I) as a substrate is 8.5–9.0;

Formula I when 10 mM Tris-HCl buffer solution (pH 7.0–9.0) is used for hydrolysis of the above substrate at 4° C., remaining activity after 48 hours is about 100%; when 10 mM of phosphate buffer solution (pH 6.0) is used, the remaining activity is about 45%; and when 10 mM of phosphate buffer solution (pH 5.0) is used, the remaining activity is about 20%;

(4) Optimum temperature and heat stability:
   optimum temperature for hydrolysis in the case of using p-nitrophenyl ester of 2,2-dimethyl-3-(2,2-dichlorovinyl)-cyclopropane carboxylic acid as a substrate in 100 mM Tris-HCl buffer (pH 9.0) is 50°–55° C.;
   remaining activities after treating in 100 mM Tris-HCl buffer solution (pH 9.0) for 10 minutes at 35° C., is about 100%, at 40° C. about 80%, and at 50° C. about 15%;

(5) Molecular weight:
   54,00±2,000 (by gel filtration and SDS polyacrylamide gel electrophoresis)

(6) Isoelectric point: 4.8±0.1

(7) Inactivating conditions:
   (a) completely inactivated by treatment with 100 μM phenylmethylsulfonyl fluoride or 80 μM diisopropyl fluorophosphate at 37° C. for 10 minutes;
   (b) activity decreased about 25% and about 70% by treatment with 100 mM Tris-HCl buffer solution (pH 9.0) containing 1 mM sodium deoxycholate and 5 mM sodium lauryl sulfate, respectively, at 37° C. for 10 minutes.

* * * * *